US012788634B2

(12) United States Patent
Adler et al.

(10) Patent No.: US 12,788,634 B2
(45) Date of Patent: Nov. 10, 2026

(54) MICRO-DEVICES FOR TREATMENT OF AN EYE

(71) Applicant: Avedro, Inc., Waltham, MA (US)

(72) Inventors: Desmond Christopher Adler, Bedford, MA (US); Reza Zadno, San Francisco, CA (US); Paul Bavier, Cambridge, MA (US); David C. Iannetta, Campbridge, MA (US); Jun Zhang, Lexington, MA (US)

(73) Assignee: Avedro, Inc., Burlington, MA (US)

( * ) Notice: Subject to any disclaimer, the term of this patent is extended or adjusted under 35 U.S.C. 154(b) by 0 days.

(21) Appl. No.: 18/471,950

(22) Filed: Sep. 21, 2023

(65) Prior Publication Data

US 2024/0009031 A1 Jan. 11, 2024

Related U.S. Application Data

(63) Continuation of application No. 16/979,088, filed as application No. PCT/US2019/021436 on Mar. 8, 2019, now Pat. No. 11,766,356.

(60) Provisional application No. 62/640,243, filed on Mar. 8, 2018.

(51) Int. Cl.
*A61F 9/008* (2006.01)

(52) U.S. Cl.
CPC .... *A61F 9/008* (2013.01); *A61F 2009/00872* (2013.01)

(58) Field of Classification Search
CPC ............ A61F 9/008; A61F 2009/00872; A61F 9/0079
See application file for complete search history.

(56) References Cited

U.S. PATENT DOCUMENTS

| | | | | |
|---|---|---|---|---|
| 6,096,066 A * | 8/2000 | Chen | A61N 5/062 607/91 |
| 11,766,356 B2 * | 9/2023 | Adler | A61F 9/0079 606/5 |
| 2005/0015121 A1 * | 1/2005 | Molina | A61N 5/0616 607/88 |

(Continued)

FOREIGN PATENT DOCUMENTS

WO WO-2016177600 A1 * 11/2016 ........... A61B 18/148

*Primary Examiner* — Niketa Patel
*Assistant Examiner* — Sebastian X Lukjan
(74) *Attorney, Agent, or Firm* — K&L Gates LLP

(57) ABSTRACT

A micro-device for corneal cross-linking treatment includes a body including an outer portion and an inner portion. The inner portion is coupled to the outer portion which is disposed about a periphery of the inner portion. When the body is against an eye surface, the outer portion contacts the eye surface and the inner portion defines a chamber over a cornea of the eye. The micro-device includes an illumination system including a micro-optical element and an optical fiber. The micro-optical element includes micro-LEDs configured to direct photoactivating light through the inner portion to the cornea of the eye when the body is positioned against the surface of the eye. The photoactivating light generates cross-linking activity with a cross-linking agent applied to the cornea. The optical fiber couples the micro-optical element to a light source and includes a surface configured to reflect the photoactivating light to the micro-optical element.

20 Claims, 8 Drawing Sheets

(56) References Cited

U.S. PATENT DOCUMENTS

| | | | | | |
|---|---|---|---|---|---|
| 2006/0290883 | A1* | 12/2006 | Rosenthal | G02C 7/047 | 351/159.12 |
| 2007/0233208 | A1* | 10/2007 | Kurtz | A61N 5/0613 | 607/88 |
| 2008/0015660 | A1* | 1/2008 | Herekar | A61N 5/062 | 607/88 |
| 2010/0057060 | A1* | 3/2010 | Herekar | A61F 9/008 | 606/4 |
| 2012/0069413 | A1* | 3/2012 | Schultz | G02B 27/0101 | 359/240 |
| 2013/0211389 | A1* | 8/2013 | Chuck | A61P 27/02 | 606/5 |
| 2014/0268042 | A1* | 9/2014 | Bor | A61B 3/1005 | 351/246 |
| 2016/0067086 | A1* | 3/2016 | Tedford | A61N 5/0613 | 606/4 |
| 2016/0175147 | A1* | 6/2016 | Lopath | A61N 5/062 | 604/20 |

* cited by examiner

MICRO-DEVICES FOR TREATMENT OF AN EYE

CROSS REFERENCE TO RELATED APPLICATIONS

This application is a continuation of U.S. application Ser. No. 16/979,088 filed Sep. 8, 2020, which incorporates by reference and claims the benefit of priority to National Stage Application of International Patent Application No. PCT/US2019/021436, filed Mar. 8, 2019, which claims priority to and the benefit of U.S. Provisional Application No. 62/640,243, filed Mar. 8, 2018, the contents of these applications being incorporated entirely herein by reference.

BACKGROUND

Field

The present disclosure pertains to systems and methods for eye treatments, and more particularly, to systems and methods employ an integrated micro-device that can deliver a drug, photoactivating light, and/or oxygen for a corneal cross-linking treatment.

Description of Related Art

Cross-linking treatments may be employed to treat eyes suffering from disorders, such as keratoconus. In particular, keratoconus is a degenerative disorder of the eye in which structural changes within the cornea cause it to weaken and change to an abnormal conical shape. Cross-linking treatments can strengthen and stabilize areas weakened by keratoconus and prevent undesired shape changes.

Cross-linking treatments may also be employed after surgical procedures, such as Laser-Assisted in situ Keratomileusis (LASIK) surgery. For instance, a complication known as post-LASIK ectasia may occur due to the thinning and weakening of the cornea caused by LASIK surgery. In post-LASIK ectasia, the cornea experiences progressive steepening (bulging). Accordingly, cross-linking treatments can strengthen and stabilize the structure of the cornea after LASIK surgery and prevent post-LASIK ectasia.

Cross-linking treatments may also be employed to induce refractive changes in the cornea to correct disorders such as myopia, hyperopia, myopia, hyperopia, astigmatism, irregular astigmatism, presbyopia, etc.

SUMMARY

Embodiments employ a micro-device (e.g., form factor of a scleral contact lens) that can integrate delivery of a cross-linking agent, photoactivating light, and/or oxygen for a cross-linking treatment. For instance, embodiments can: (i) provide enhanced oxygen delivery to the cornea by employing selected materials, micro-channels, and/or integrated micro-tubing; (ii) provide more uniform delivery of photoactivating light to the cornea by employing optical fibers coupled to an external light source and/or micro-LED's integrated directly with the treatment micro-device; (iii) provide controllable delivery of photoactivating light to the cornea by employing individually addressable micro-LED arrays and/or spatial light modulators, which may be integrated directly with the treatment micro-device; and/or (iv) provide for delivery of any predetermined pattern of photoactivating light to the cornea by employing light absorption and/or reflection pattern(s), and/or employing a diffractive optical element (DOE) with fiber-coupled laser delivery.

Advantageously, embodiments do not require the use of an eyelid speculum to hold the eye open throughout the procedure and as such reduce patient discomfort associated with use of the eyelid speculum. Additionally, the patient may be seated upright during the procedure. Such embodiments can simplify clinical workflow by requiring substantially less intervention and/or monitoring by the practitioner during the cross-linking procedure, e.g., to ensure proper delivery of photoactivating light, proper eye hydration, etc. Furthermore, capital cost may also be significantly reduced compared to systems that require complex optics, electronics, sophisticated eye tracking technology, etc.

According to an example embodiment, a micro-device for corneal cross-linking treatment includes a body including an outer portion and an inner portion. The outer portion is disposed about a periphery of the inner portion. The inner portion is shaped such that, when the body is positioned against a surface of an eye, the outer portion contacts the surface of the eye surface and the inner portion defines a chamber over a cornea of the eye. The micro-device includes an illumination system including a micro-optical element coupled to the body. The micro-optical element is configured to direct photoactivating light to the cornea of the eye when the body is positioned against the surface of the eye. The photoactivating light generates cross-linking activity with a cross-linking agent applied to the cornea. In some cases, the chamber may be configured to receive a cross-linking agent to soak a cornea of the eye.

According to another example embodiment, a system for corneal cross-linking treatment includes a micro-device including a body including an outer portion and an inner portion. The outer portion is disposed about a periphery of the inner portion. The inner portion is shaped such that, when the body is positioned against a surface of an eye, the outer portion contacts the surface of the eye and the inner portion defines a chamber over a cornea of the eye. The system includes an oxygen delivery mechanism configured to provide at least partially an enclosure for the micro-device. The enclosure receives oxygen from an oxygen source to surround the micro-device with oxygen. The oxygen enhances cross-linking activity generated by a cross-linking agent applied to the cornea. The body of the microdevice is configured to allow the oxygen in the enclosure to enter the chamber when the body is positioned against a surface of an eye.

Figure 1:
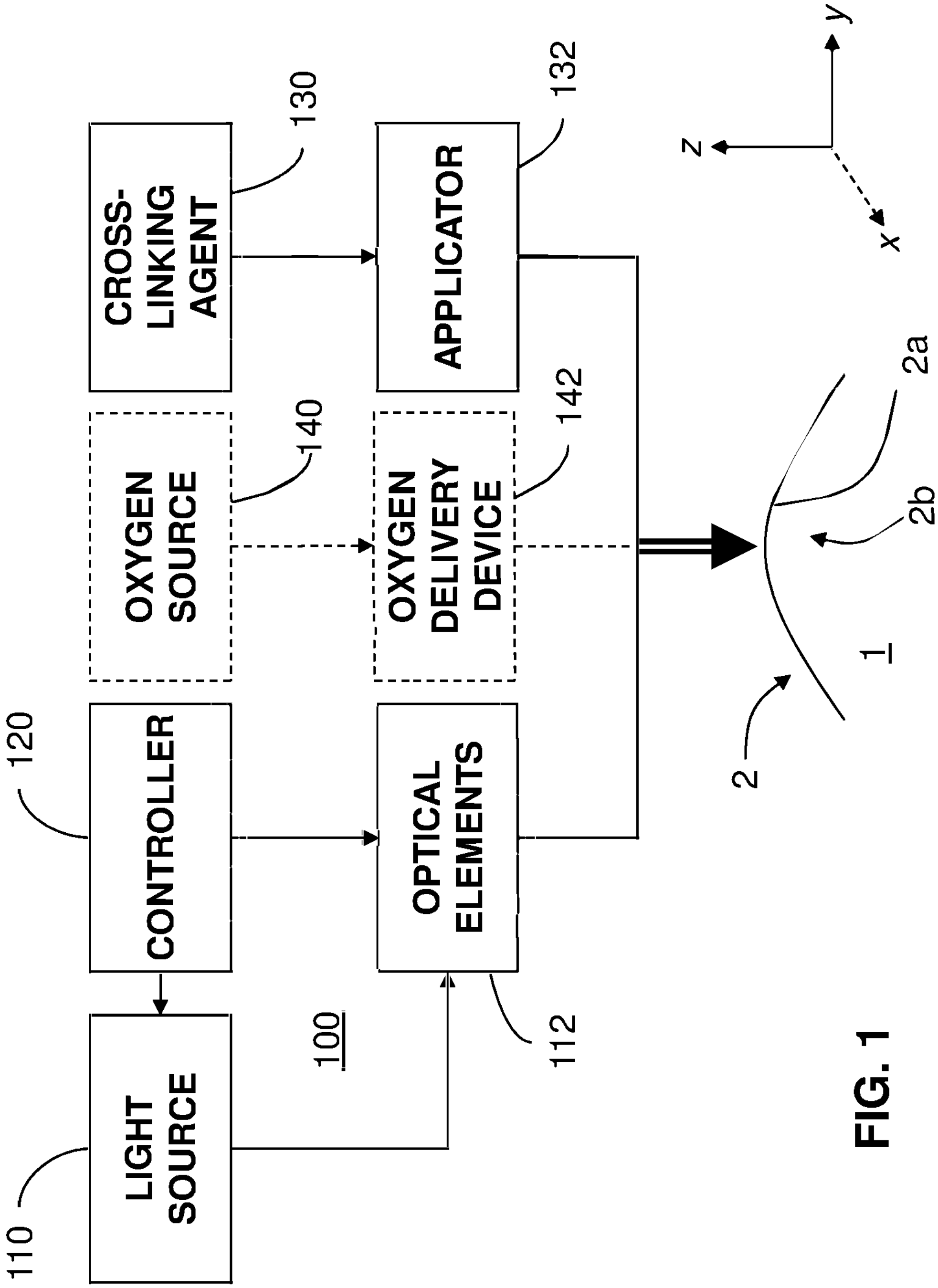
FIG. 1 illustrates an example system that delivers a cross-linking agent, photoactivating light, and oxygen to a cornea of an eye in order to generate cross-linking of corneal collagen, according to aspects of the present disclosure.

While the present disclosure is susceptible to various modifications and alternative forms, a specific embodiment thereof has been shown by way of example in the drawings and will herein be described in detail. It should be understood, however, that it is not intended to limit the present disclosure to the particular forms disclosed, but on the contrary, the intention is to cover all modifications, equivalents, and alternatives falling within the spirit of the present disclosure.

DESCRIPTION

FIG. 1 illustrates an example treatment system 100 for generating cross-linking of collagen in a cornea 2 of an eye 1. The treatment system 100 includes an applicator 132 for applying a cross-linking agent 130 to the cornea 2. In example embodiments, the applicator 132 may be an eye dropper, syringe, or the like that applies the photosensitizer 130 as drops to the cornea 2. Example systems and methods for applying the cross-linking agent is described in U.S. Patent Application Publication No. 2017/0296383, filed Apr. 13, 2017 and titled "Systems and Methods for Delivering Drugs to an Eye," the contents of which are incorporated entirely herein by reference.

The cross-linking agent 130 may be provided in a formulation that allows the cross-linking agent 130 to pass through the corneal epithelium 2*a* and to underlying regions in the corneal stroma 2*b*. Alternatively, the corneal epithelium 2*a* may be removed or otherwise incised to allow the cross-linking agent 130 to be applied more directly to the underlying tissue.

The treatment system 100 includes an illumination system with a light source 110 and optical elements 112 for directing light to the cornea 2. The light causes photoactivation of the cross-linking agent 130 to generate cross-linking activity in the cornea 2. For example, the cross-linking agent may include riboflavin and the photoactivating light may include ultraviolet A (UVA) (e.g., approximately 365 nm) light. Alternatively, the photoactivating light may include another wavelength, such as a visible wavelength (e.g., approximately 452 nm). As described further below, corneal cross-linking improves corneal strength by creating chemical bonds within the corneal tissue according to a system of photochemical kinetic reactions. For instance, riboflavin and the photoactivating light may be applied to stabilize and/or strengthen corneal tissue to address diseases such as keratoconus or post-LASIK ectasia.

The treatment system 100 includes one or more controllers 120 that control aspects of the treatment system 100, including the light source 110 and/or the optical elements 112. In an implementation, the cornea 2 can be more broadly treated with the crosslinking agent 130 (e.g., with an eye dropper, syringe, etc.), and the photoactivating light from the light source 110 can be selectively directed to regions of the treated cornea 2 according to a particular pattern.

The optical elements 112 may include one or more mirrors or lenses for directing and focusing the photoactivating light emitted by the light source 110 to a particular pattern on the cornea 2. The optical elements 112 may further include filters for partially blocking wavelengths of light emitted by the light source 110 and for selecting particular wavelengths of light to be directed to the cornea 2 for photoactivating the cross-linking agent 130. In addition, the optical elements 112 may include one or more beam splitters for dividing a beam of light emitted by the light source 110, and may include one or more heat sinks for absorbing light emitted by the light source 110. The optical elements 112 may also accurately and precisely focus the photo-activating light to particular focal planes within the cornea 2, e.g., at a particular depths in the underlying corneal stroma 2*b* where cross-linking activity is desired.

Moreover, specific regimes of the photoactivating light can be modulated to achieve a desired degree of cross-linking in the selected regions of the cornea 2. The one or more controllers 120 may be used to control the operation of the light source 110 and/or the optical elements 112 to precisely deliver the photoactivating light according to any combination of: wavelength, bandwidth, intensity, power, location, depth of penetration, and/or duration of treatment (the duration of the exposure cycle, the dark cycle, and the ratio of the exposure cycle to the dark cycle duration).

The parameters for photoactivation of the cross-linking agent 130 can be adjusted, for example, to reduce the amount of time required to achieve the desired cross-linking. In an example implementation, the time can be reduced from minutes to seconds. While some configurations may apply the photoactivating light at an irradiance of 5 $mW/cm^2$, larger irradiance of the photoactivating light, e.g., multiples of 5 $mW/cm^2$, can be applied to reduce the time required to achieve the desired cross-linking. The total dose of energy absorbed in the cornea 2 can be described as an effective dose, which is an amount of energy absorbed through an area of the corneal epithelium 2*a*. For example the effective dose for a region of the corneal surface 2A can be, for example, 5 J/cm, or as high as 20 J/cm or 30 $J/cm^2$. The effective dose described can be delivered from a single application of energy, or from repeated applications of energy.

The optical elements 112 of the treatment system 100 may include a microelectromechanical system (MEMS) device, e.g., a digital micro-mirror device (DMD), to modulate the application of photoactivating light spatially and temporally. Using DMD technology, the photoactivating light from the light source 110 is projected in a precise spatial pattern that is created by microscopically small mirrors laid out in an array on a semiconductor chip. Each mirror represents one or more pixels in the pattern of projected light. With the DMD one can perform topography guided cross-linking. The control of the DMD according to topography may employ several different spatial and temporal irradiance and dose profiles. These spatial and temporal dose profiles may be created using continuous wave illumination but may also be modulated via pulsed illumination by pulsing the illumination source under varying frequency and duty cycle regimes. Alternatively, the DMD can modulate different frequencies and duty cycles on a pixel by pixel basis to give ultimate flexibility using continuous wave illumination. Or alternatively, both pulsed illumination and modulated DMD frequency and duty cycle combinations may be combined.

This allows for specific amounts of spatially determined corneal cross-linking. This spatially determined cross-linking may be combined with dosimetry, interferometry, optical coherence tomography (OCT), corneal topography, etc., for pre-treatment planning and/or real-time monitoring and modulation of corneal cross-linking during treatment. Aspects of a dosimetry system are described in further detail below. Additionally, pre-clinical patient information may be combined with finite element biomechanical computer modeling to create patient specific pre-treatment plans.

To control aspects of the delivery of the photoactivating light, embodiments may also employ aspects of multiphoton excitation microscopy. In particular, rather than delivering a single photon of a particular wavelength to the cornea 2, the treatment system 100 may deliver multiple photons of longer wavelengths, i.e., lower energy, that combine to initiate the cross-linking. Advantageously, longer wavelengths are scattered within the cornea 2 to a lesser degree than shorter wavelengths, which allows longer wavelengths of light to penetrate the cornea 2 more efficiently than light of shorter wavelengths. Shielding effects of incident irradiation at deeper depths within the cornea are also reduced over conventional short wavelength illumination since the absorption of the light by the photosensitizer is much less at the longer wavelengths. This allows for enhanced control over depth specific cross-linking. For example, in some embodiments, two photons may be employed, where each photon carries approximately half the energy necessary to excite the molecules in the cross-linking agent 130 to generate the photochemical kinetic reactions described further below. When a cross-linking agent molecule simultaneously absorbs both photons, it absorbs enough energy to release reactive radicals in the corneal tissue. Embodiments may also utilize lower energy photons such that a cross-linking agent molecule must simultaneously absorb, for example, three, four, or five, photons to release a reactive radical. The probability of the near-simultaneous absorption of multiple photons is low, so a high flux of excitation photons may be required, and the high flux may be delivered through a femtosecond laser.

A large number of conditions and parameters affect the cross-linking of corneal collagen with the cross-linking agent 130. For example, the irradiance and the dose of photoactivating light affect the amount and the rate of cross-linking.

When the cross-linking agent 130 is riboflavin in particular, the UVA light may be applied continuously (continuous wave (CW)) or as pulsed light, and this selection has an effect on the amount, the rate, and the extent of cross-linking. If the UVA light is applied as pulsed light, the duration of the exposure cycle, the dark cycle, and the ratio of the exposure cycle to the dark cycle duration have an effect on the resulting corneal stiffening. Pulsed light illumination can be used to create greater or lesser stiffening of corneal tissue than may be achieved with continuous wave illumination for the same amount or dose of energy delivered. Light pulses of suitable length and frequency may be used to achieve more optimal chemical amplification. For pulsed light treatment, the on/off duty cycle may be between approximately 1000/1 to approximately 1/1000; the irradiance may be between approximately 1 mW/cm—to approximately 1000 mW/cm—average irradiance, and the pulse rate may be between approximately 0.01 HZ to approximately 1000 Hz or between approximately 1000 Hz to approximately 100,000 Hz.

The treatment system 100 may generate pulsed light by employing a DMD, electronically turning the light source 110 on and off, and/or using a mechanical or optoelectronic (e.g., Pockels cells) shutter or mechanical chopper or rotating aperture. Because of the pixel specific modulation capabilities of the DMD and the subsequent stiffness impartment based on the modulated frequency, duty cycle, irradiance and dose delivered to the cornea, complex biomechanical stiffness patterns may be imparted to the cornea to allow for various amounts of refractive correction. These refractive corrections, for instance, may involve combinations of myopia, hyperopia, astigmatism, irregular astigmatism, presbyopia and complex corneal refractive surface corrections because of ophthalmic conditions such as keratoconus, pellucid marginal disease, post-LASIK ectasia, and other conditions of corneal biomechanical alteration/degeneration, etc. A specific advantage of the DMD system and method is that it allows for randomized asynchronous pulsed topographic patterning, creating a non-periodic and uniformly appearing illumination which eliminates the possibility for triggering photosensitive epileptic seizures or flicker vertigo for pulsed frequencies between 2 Hz and 84 Hz.

Although example embodiments may employ stepwise on/off pulsed light functions, it is understood that other functions for applying light to the cornea may be employed to achieve similar effects. For example, light may be applied to the cornea according to a sinusoidal function, sawtooth function, or other complex functions or curves, or any combination of functions or curves. Indeed, it is understood that the function may be substantially stepwise where there may be more gradual transitions between on/off values. In addition, it is understood that irradiance does not have to decrease down to a value of zero during the off cycle, and may be above zero during the off cycle. Desired effects may be achieved by applying light to the cornea according to a curve varying irradiance between two or more values.

Examples of systems and methods for delivering photoactivating light are described, for example, in U.S. Patent Application Publication No. 2011/0237999, filed Mar. 18, 2011 and titled "Systems and Methods for Applying and Monitoring Eye Therapy," U.S. Patent Application Publication No. 2012/0215155, filed Apr. 3, 2012 and titled "Systems and Methods for Applying and Monitoring Eye Therapy," and U.S. Patent Application Publication No. 2013/0245536, filed Mar. 15, 2013 and titled "Systems and Methods for Corneal Cross-Linking with Pulsed Light," the contents of these applications being incorporated entirely herein by reference.

The addition of oxygen also affects the amount of corneal stiffening. In human tissue, O2 content is very low compared to the atmosphere. The rate of cross-linking in the cornea, however, is related to the concentration of O2 when it is irradiated with photoactivating light. Therefore, it may be advantageous to increase or decrease the concentration of O2 actively during irradiation to control the rate of cross-linking until a desired amount of cross-linking is achieved. Oxygen may be applied during the cross-linking treatments in a number of different ways. One approach involves supersaturating the riboflavin with O2 Thus, when the riboflavin is applied to the eye, a higher concentration of O2 is delivered directly into the cornea with the riboflavin and affects the reactions involving O2 when the riboflavin is exposed to the photoactivating light. According to another approach, a steady state of O2 (at a selected concentration) may be maintained at the surface of the cornea to expose the cornea to a selected amount of O2 and cause O2 to enter the cornea. As shown in FIG. 1, for instance, the treatment system 100 also includes a oxygen source 140 and an oxygen delivery device 142 that optionally delivers oxygen at a selected concentration to the cornea 2. Example systems and methods for applying oxygen during cross-linking treatments are described, for example, in U.S. Pat. No. 8,574,277, filed Oct. 21, 2010 and titled "Eye Therapy," U.S. Patent Application Publication No. 2013/0060187, filed Oct. 31, 2012 and titled "Systems and Methods for Corneal CrossLinking with Pulsed Light," the contents of these applications being incorporated entirely herein by reference. Additionally, an example mask device for delivering concentrations of oxygen as well as photoactivating light in eye treatments is described in U.S. Patent Application Publication No. 2017/0156926, filed Dec. 3, 2016 and titled "Systems and Methods for Treating an Eye with a Mask Device," the contents of which are incorporated entirely herein by reference. For instance, a mask may be placed over the eye(s) to produce a consistent and known oxygen concentration above the surface.

When riboflavin absorbs radiant energy, especially light, it undergoes photoactivation. There are two photochemical kinetic pathways for riboflavin photoactivation, Type I and Type II. The reactions involved in both the Type I and Type II mechanisms and other aspects of the photochemical kinetic reactions generating cross-linking activity are described in U.S. Patent Application Publication No. 2016/0310319, filed Apr. 27, 2016 and titled "Systems and Methods for Cross-Linking Treatments of an Eye," the contents of which are incorporated entirely herein by reference.

According to an example embodiment of the treatment system 100 described above, the applicator 132 is a syringe that applies the cross-linking agent 130 to the cornea 2 while the eye I is held open with an eyelid speculum. After the cornea 2 has been soaked with the cross-linking agent 130 for approximately one minute to approximately twenty minutes, photoactivating light is delivered from a separate illumination system, which includes the light source 110 and optical elements 112. The illumination system may be supported on a mobile cart or mounted on a table to deliver the photoactivating light to the cornea 2 from a working distance of several centimeters above the eye 1. In addition, the oxygen delivery device 142 is a separate device shaped like a pair of goggles that can be positioned on the head of the subject to provide at least a partial enclosure for oxygen over the eye 1. The oxygen delivery device 142 is coupled to the oxygen source 140.

Figure 2:
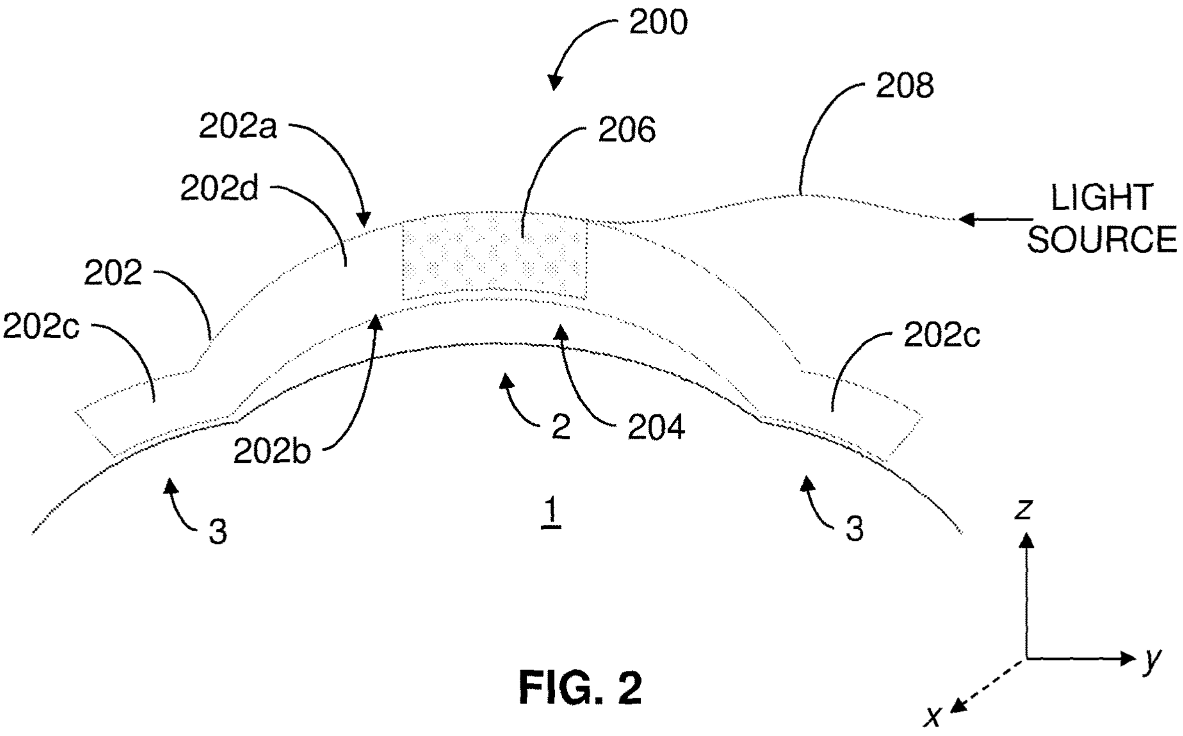
FIG. 2 illustrates a cross-sectional view of an example treatment micro-device that delivers a cross-linking agent and photoactivating light to a cornea of an eye to generate cross-linking of corneal tissue, according to aspects of the present disclosure.

FIG. 2 illustrates a cross-sectional view of an example treatment device 200 that has the form factor of a scleral contact lens. In contrast to the previous embodiment of the treatment system 100, the treatment device 200 is more compact and conveniently integrates aspects of a cross-linking procedure. The form factor for the treatment device 200 is defined by a body 202 configured to fit against an eye 1 of a subject. The body 202 includes an anterior surface 202*a* that faces away from the eye I and a posterior surface 202*b* that faces the eye 1. The body 202 may have a substantially circular shape along an x-y plane as shown in FIG. 2. The body 202 has an annular outer portion 202*c* and an inner portion 202*d* disposed within the outer portion 202*c* (i.e., the outer portion 202*c* is disposed about a periphery of the inner portion 202*d*). The outer portion 202*c*, which may be formed from a polymer, contacts a sclera 3 of the eye 1. Supported by the outer portion 202*c*, the inner portion 202*d* defines a chamber 204 over a cornea 2 of the eye 1. The chamber 204 is disposed between the surface of the cornea 2 and the posterior surface 202*b* of the body 202. As shown in FIG. 2, the inner portion 202*d* has a concave shape such that, when the body 202 is positioned against a surface of the eye 1, the outer portion 202*c* contacts the surface and the chamber 204 defined by the inner portion 202*d* is positioned over the cornea 2.

During a procedure, the chamber 204 can be filled with a cross-linking agent to allow the cornea 2 to soak. In some cases, the chamber 204 may be filled with another drug and/or a hydrating fluid. Due to the fit of the outer portion 202*c* against the sclera 3, the cross-linking agent does not leak from the chamber 204. Advantageously, the cross-linking agent can be delivered to the cornea 2 without the use of an eyelid speculum. Thus, the subject does not experience the typical discomfort associated with use of an eyelid speculum and can sit more comfortably upright during the procedure.

The treatment device 200 also includes a micro-optical element 206 and an optical fiber 208. The micro-optical element 206 is coupled to the body 202. The optical fiber 208 couples the micro-optical element 206 to a light source. During a procedure, photoactivating light travels from the light source to the micro-optical element 206 via the optical fiber 208. The micro-optical element 206 is configured to focus the photoactivating light to a desired transverse plane (x-y plane) in the cornea 2. Due to the fit of body 202 against the eye 1, the body 202 does not move relative to the eye 1 even if the eye 1 moves and/or the subject blinks. As such, the micro-optical element 206 remains stably positioned over the cornea 2 and the photoactivating light can be delivered to desired areas of the cornea 2. In other words, active eye tracking is not required as adjustments in response to eye movement and/or blinking are not required.

Although the treatment device 200 may integrate features for delivering the crosslinking agent and the photoactivating light, the body 202 may inhibit gas flow to the eye 1 and thus limit the amount of oxygen available at the corneal surface. Other treatment devices, however, are configured to provide elevated oxygen concentrations that promote cross-linking activity and decrease treatment times.

Figure 3:
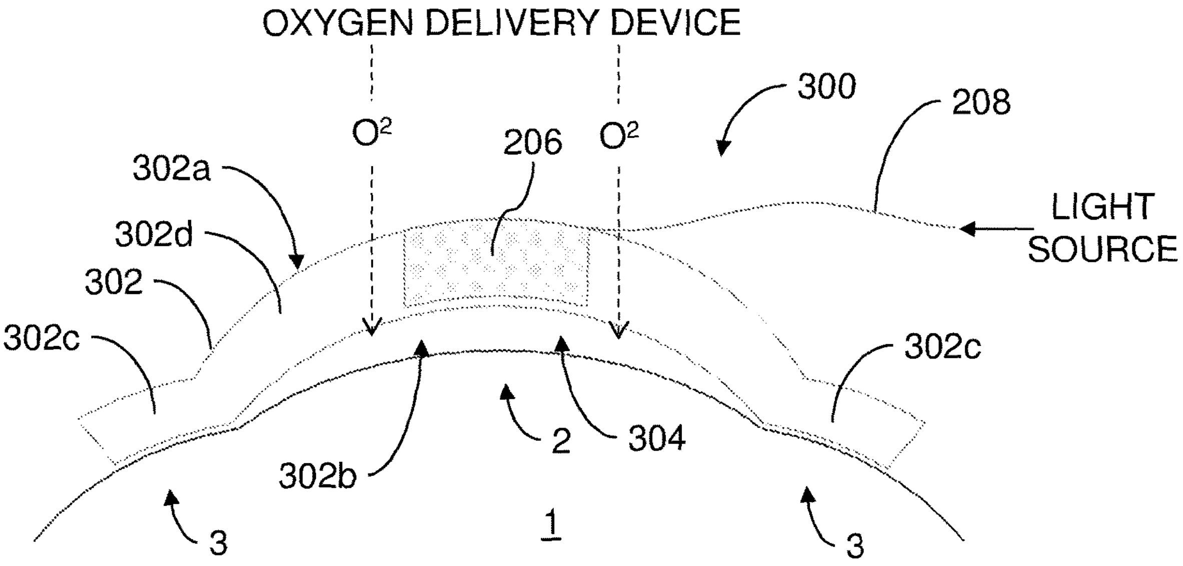
FIG. 3 illustrates a cross-sectional view of another example treatment microdevice that includes a body formed from an oxygen-permeable material to provide elevated oxygen concentrations for cross-linking activity, according to aspects of the present disclosure.

For instance, FIG. 3 illustrates another example treatment device 300 that includes a body 302 formed from an oxygen-permeable material, such as silicone, a silicone hydrogel, or other oxygen-permeable polymer. Like the treatment device 200, the treatment device 300 has the form factor of a sclera] contact lens and is configured to fit against an eye 1 of a subject. The body 302 includes an anterior surface 302*a* that faces away from the eye 1 and a posterior surface 302*b* that faces the eye 1. The body 302 has an annular outer portion 302*c* and an inner portion 302*d* disposed within the outer portion 302*c*. The outer portion 202*c* contacts a sclera 3 of the eye 1, and the inner portion 302*d* defines a chamber 304 over a cornea 2. The chamber 304 may be filled with a cross-linking agent for delivery to the cornea 2. The treatment device 300 also includes the optical fiber 208 and the micro-optical element 206 as described above. As such, the treatment device 300 may be implemented like the treatment device 200.

A separate external oxygen delivery device, however, may be additionally employed with the treatment device 300. In particular, the oxygen delivery device can provide an oxygen-rich environment (e.g., O2 saturation>90%) immediately surrounding the eye 1. Oxygen from the oxygen delivery device can flow through the oxygen-permeable material of the body 302 and to the cornea 2 during a procedure. In some embodiments, the oxygen delivery device is shaped like a pair of goggles that can be positioned on the head to provide at least a partial enclosure for oxygen surrounding the treatment device 300 which is positioned on the eye 1.

Figure 4:
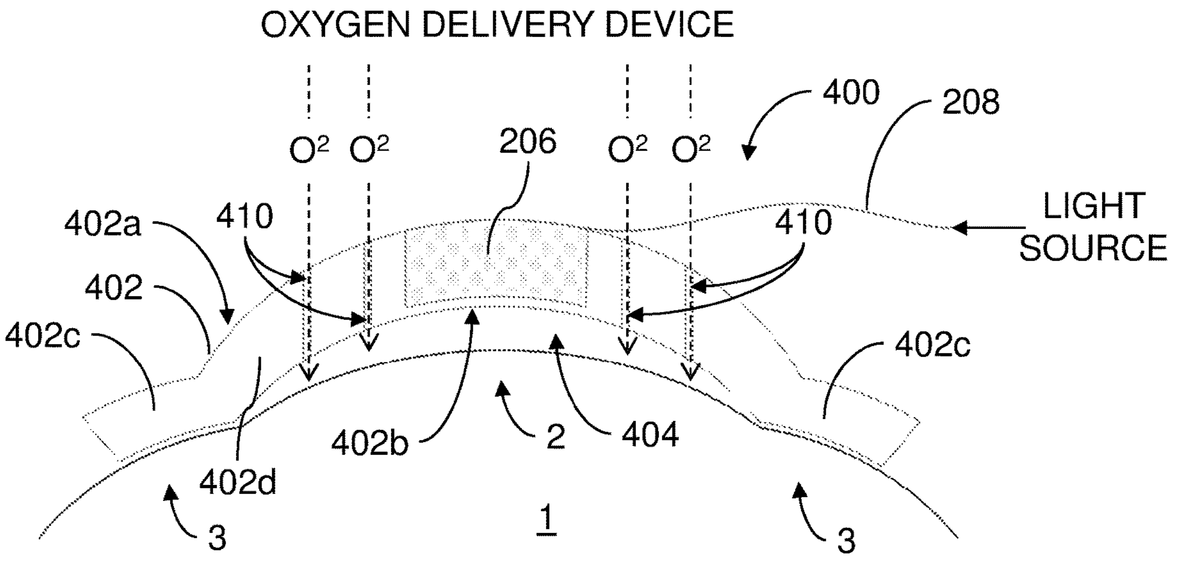
FIG. 4 illustrates yet another example treatment micro-device that includes a body with micro-channels to provide elevated oxygen concentrations for cross-linking activity, according to aspects of the present disclosure.

FIG. 4 illustrates yet another example treatment device 400 that is also configured to provide elevated oxygen concentrations to promote cross-linking activity and decrease treatment times. In particular, the treatment device 400 includes a body 402 with one or more micro-channels 410 that allow oxygen to pass through the body 402 to a cornea 2. Like the treatment device 200, the treatment device 400 has the form factor of a scleral contact lens and is configured to fit against an eye 1 of a subject. The body 402 includes an anterior surface 402*a* that faces away from the eye 1 and a posterior surface 402*b* that faces the eye 1. The body 402 has an annular outer portion 402*c* and an inner portion 402*d* disposed within the outer portion 402*c*. The outer portion 402*c* contacts a sclera 3 of the eye 1, and the inner portion 402*d* defines a chamber 404 over a cornea 2. The chamber 404 may be filled with a cross-linking agent for delivery to the cornea 2. The treatment device 400 also includes the optical fiber 208 and the micro-optical element 206 as described above. As such, the treatment device 400 may be implemented like the treatment device 200.

A separate external oxygen delivery device, however, may be additionally employed with the treatment device 400. In particular, the oxygen delivery device can provide an oxygen-rich environment (e.g., O2 saturation>90%) immediately surrounding the eye 1. The one or more micro-channels 410 extend from the anterior surface 402*a* to the chamber 404. As such, oxygen from the oxygen delivery device can flow through the one or more micro-channels 410 and to the cornea 2 during a procedure. In some embodiments, the oxygen delivery device is shaped like a pair of goggles that can be positioned on the head to provide at least a partial enclosure for oxygen surrounding the treatment device 400 which is positioned on the eye 1. Rather than forming the body 402 from an oxygen-permeable material, the body 402 may be more conveniently formed from a greater range of materials that may be more amenable to the integration of other optical, opto-electrical, or mechanical features.

Figure 5:
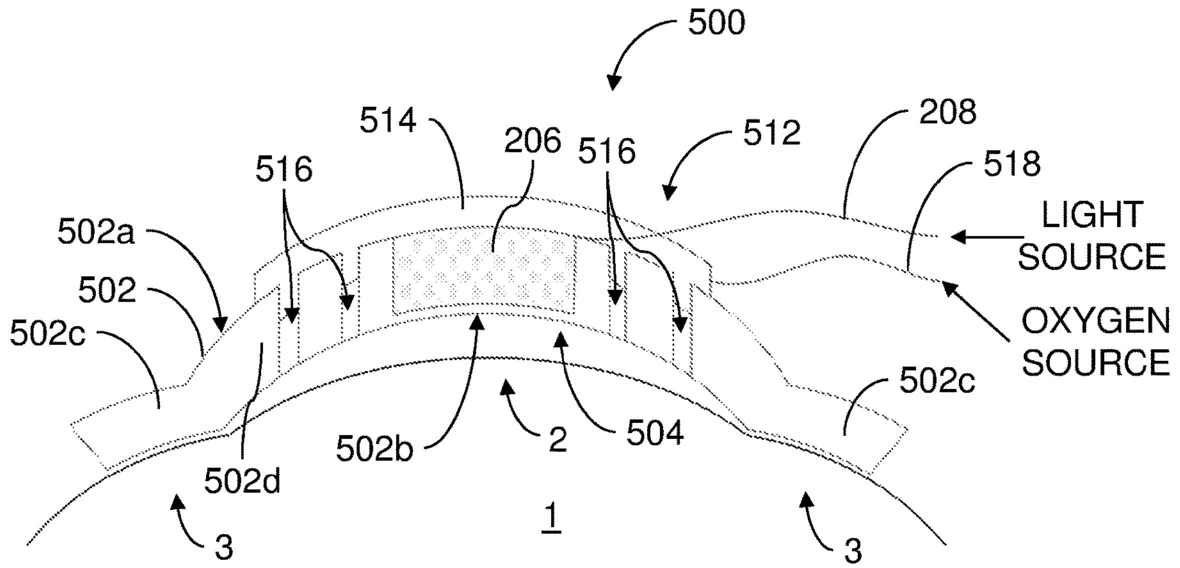
FIG. 5 illustrates a further example treatment micro-device that includes an integrated oxygen delivery mechanism with a closed-loop oxygen path to provide elevated oxygen concentrations for cross-linking activity, according to aspects of the present disclosure.

FIG. 5 illustrates a further example treatment device 500 that is also configured to provide elevated oxygen concentrations to promote cross-linking activity and decrease treatment times. In contrast to the use of the treatment devices 300 and 400, the treatment device 500 is not employed with a separate external oxygen delivery device, such as the device shaped like a pair of goggles described above. Rather, an oxygen delivery mechanism 512 is integrated into the body 502 to deliver oxygen to a cornea 2.

The treatment device 500 has the form factor of a scleral contact lens and is configured to fit against an eye I of a subject. The body 502 includes an anterior surface 502*a* that faces away from the eye I and a posterior surface 502*b* that faces the eye 1. The body 502 has an annular outer portion 502*c* and an inner portion 502*d* disposed within the outer portion 502*c*. The outer portion 502*c* contacts a sclera 3 of the eye 1, and the inner portion 502*d* defines a chamber 504 over the cornea 2. The chamber 504 may be filled with a cross-linking agent for delivery to the cornea 2. The treatment device 500 also includes the optical fiber 208 and the micro-optical element 206 as described above. As such, the treatment device 500 may be implemented to deliver the cross-linking agent and photoactivating light to the cornea 2.

Additionally, the oxygen delivery mechanism 512 includes a flexible component 514 that is coupled to the body 502. The flexible component 514 may be micro-molded. The oxygen delivery mechanism 512 includes one or more micro-channels 516 that extend from the flexible component 514 and through the body 502 to the chamber 504 over the cornea 2. The oxygen delivery mechanism 512 includes a flexible tube 518 that couples the flexible component 514 to a remote oxygen supply. High-purity, humidified oxygen can flow from the remote oxygen supply to the flexible component 514 via the flexible tube 518, and through the flexible component 514 and the one or more micro-channels 516 to the cornea 2. In alternative embodiments, the flexible component 514 and the body 502 may be formed as a single unitary element. For instance, an additive manufacturing process, such as three dimensional (3D) printing, may be employed to form the flexible component 514 as a part of the body 502.

The flexible component 514 may include everted features that mate with the one or more channels 516 (e.g., micro-channels) to assist in positional alignment during assembly of the treatment device 500. The flexible component 514 may be bonded to the body 502 or may be over-molded during manufacturing. A passageway may be formed in the flexible component 514 to accommodate the optical fiber 208. As shown in FIG. 5, the oxygen path is closed-loop, so only a small positive pressure is required from the remote oxygen supply.

Figure 6:
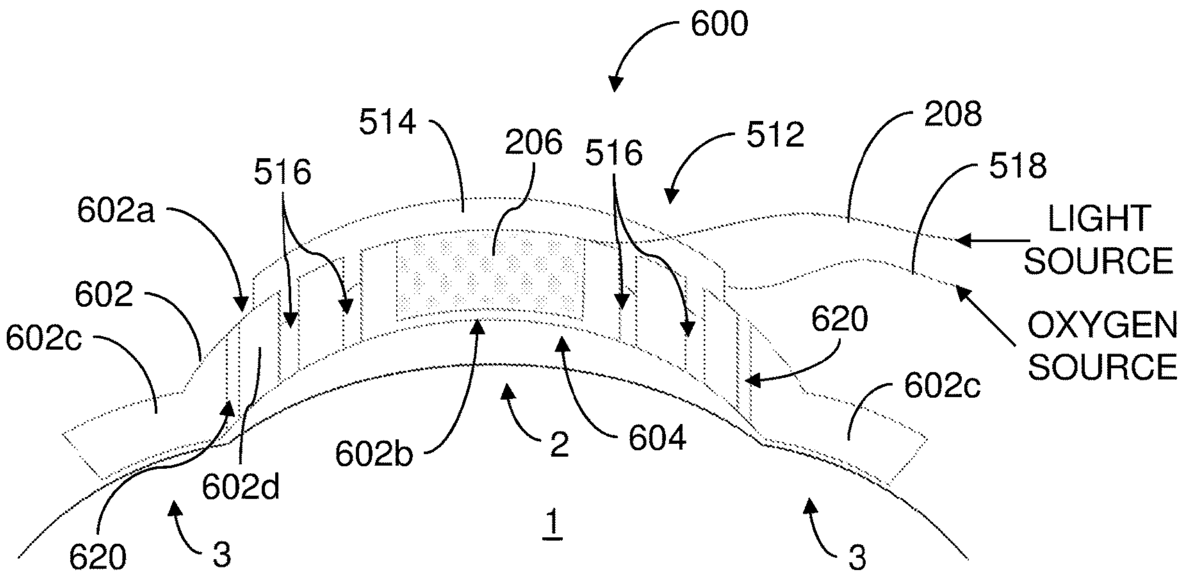
FIG. 6 illustrates another example treatment micro-device that includes an integrated oxygen delivery mechanism with an open-loop oxygen path to provide elevated oxygen concentrations for cross-linking activity, according to aspects of the present disclosure.

Alternatively, FIG. 6 illustrates another example treatment device 600 that employs an open-loop oxygen path. The treatment device 600 has the form factor of a scleral contact lens and is configured to fit against an eye 1 of a subject. The body 602 includes an anterior surface 602*a* that faces away from the eye 1 and a posterior surface 602*b* that faces the eye 1. The body 602 has an annular outer portion 602*c* and an inner portion 602*d* disposed within the outer portion 602*c*. The outer portion 602*c* contacts a sclera 3 of the eye 1, and the inner portion 602*d* defines a chamber 604 over the cornea 2. The chamber 604 may be filled with a cross-linking agent for delivery to the cornea 2. Like the treatment device 500, the treatment device 600 includes the optical fiber 208 and the micro-optical element 206 to deliver photoactivating light as described above.

Additionally, the treatment device 600 includes aspects of the oxygen delivery mechanism 512 described above. The body 602, however, also includes one or more vents 620 to create the open-loop oxygen path. The vents 620 extend through the body 602, from the chamber 604 to the anterior surface 602*a*. The delivery mechanism 512 causes oxygen to flow into the chamber 604 and to the cornea 2. The oxygen flows out of the chamber 604 through the vents 620. The open-loop oxygen path allows for continuous flow of oxygen and may be more amenable for use with conventional oxygen sources such as pressure-regulated, flow-controlled tanks or generators. Additionally, the treatment device 600 also provides enhanced protection against undesirable pressure build-up in a chamber 604. Such pressure build-up might cause the treatment device 600 to become dislodged from the eye 1 during a procedure.

As described above, prior to delivery of photoactivating light, the chamber defined by the body of a treatment device may be filled with the cross-linking agent. This is a simpler approach that eliminates the need for practitioners to apply the cross-linking agent periodically during a procedure.

As described above, the treatment device 500, 600 include the oxygen delivery mechanism 512. In particular, the oxygen delivery mechanism 512 includes the flexible tube 518 which allows oxygen to flow from the remote oxygen source to the treatment device 500, 600. To deliver a cross-linking agent and/or a hydration fluid to the cornea 2, the treatment device 500, 600 may also include a Y-valve coupled to the flexible tube 518. The Y-valve includes a first input and a second input. The first input may receive oxygen from the remote oxygen source, while the second input may receive the cross-linking agent and/or a hydration fluid from a source or applicator, such as a syringe. The Y-valve, thus, allows the practitioner to switch efficiently between the delivery of the cross-linking agent/hydration fluid and the delivery of oxygen.

Figure 7:
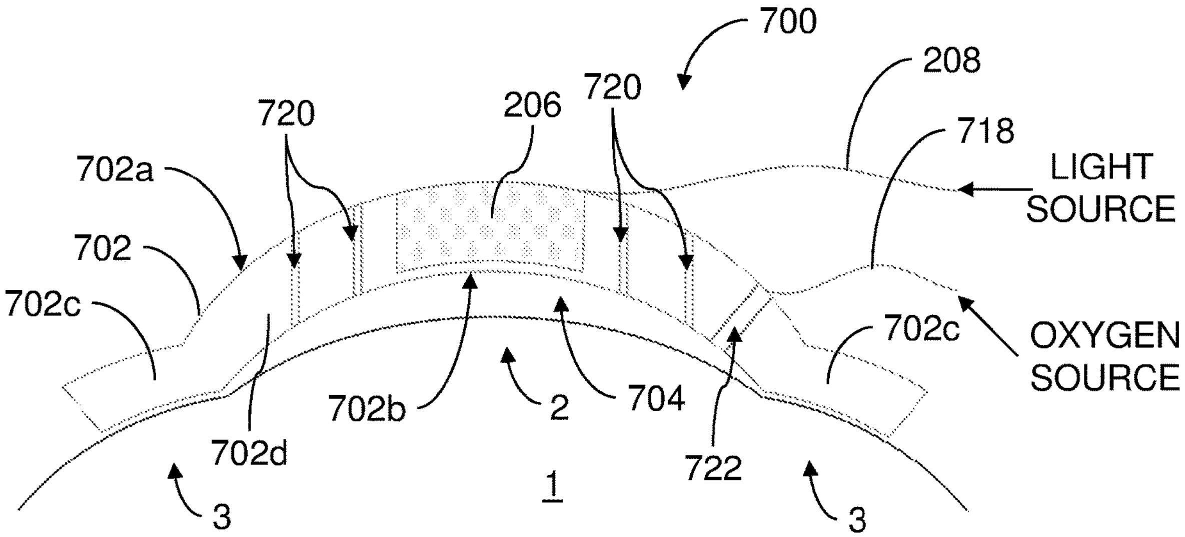
FIG. 7 illustrates yet another example treatment micro-device that includes a side channel and vents to provide elevated oxygen concentrations for cross-linking activity, according to aspects of the present disclosure.

FIG. 7 illustrates another example treatment device 700 configured to provide elevated oxygen concentrations to promote cross-linking activity and decrease treatment times. The treatment device 700 has the form factor of a scleral contact lens and is configured to fit against an eye 1 of a subject. The body 702 includes an anterior surface 702*a* that faces away from the eye 1 and a posterior surface 702*b* that faces the eye 1. The body 702 has an annular outer portion 702*c* and an inner portion 702*d* disposed within the outer portion 702*c*. The outer portion 702*c* contacts a sclera 3 of the eye 1, and the inner portion 702*d* defines a chamber 704 over the cornea 2. The chamber 704 may be filled with a cross-linking agent for delivery to the cornea 2. The treatment device 700 also includes the optical fiber 208 and the micro-optical element 206 to deliver photoactivating as described above.

The body 702 includes one or more side channels 722 that extend through the body 702 from the exterior anterior surface 702*a* to the chamber 704. The one or more side channels 722 open in the chamber 704 at the periphery of the cornea 2 (e.g., the periphery of the inner portion 702*d*). The body 702 also includes one or more vents 720 that also extend through the body 702 from the chamber 704 to the exterior anterior surface 702*a*. The treatment device 700 also includes a flexible tube 718 that couples the one or more side channels 722 to a remote oxygen source. Accordingly, oxygen can flow from the remote oxygen source through the flexible tube 718 and the one or more side channels 722 and into the chamber 704 at the periphery of the cornea 2. The flow causes the oxygen to flow/circulate over the surface of the cornea 2 before exiting the chamber 704 through the one or more vents 720.

As described above, treatment devices may employ the micro-optical element 206 and the micro-optical element 206 to deliver photoactivating light to the cornea 2. In particular, the micro-optical element 206 is configured to deliver the photoactivating light to a desired transverse plane (x-y plane) in the cornea 2. The treatment devices, however, may employ other types of optical elements that improve the delivery of the photoactivating light.

Figure 8:
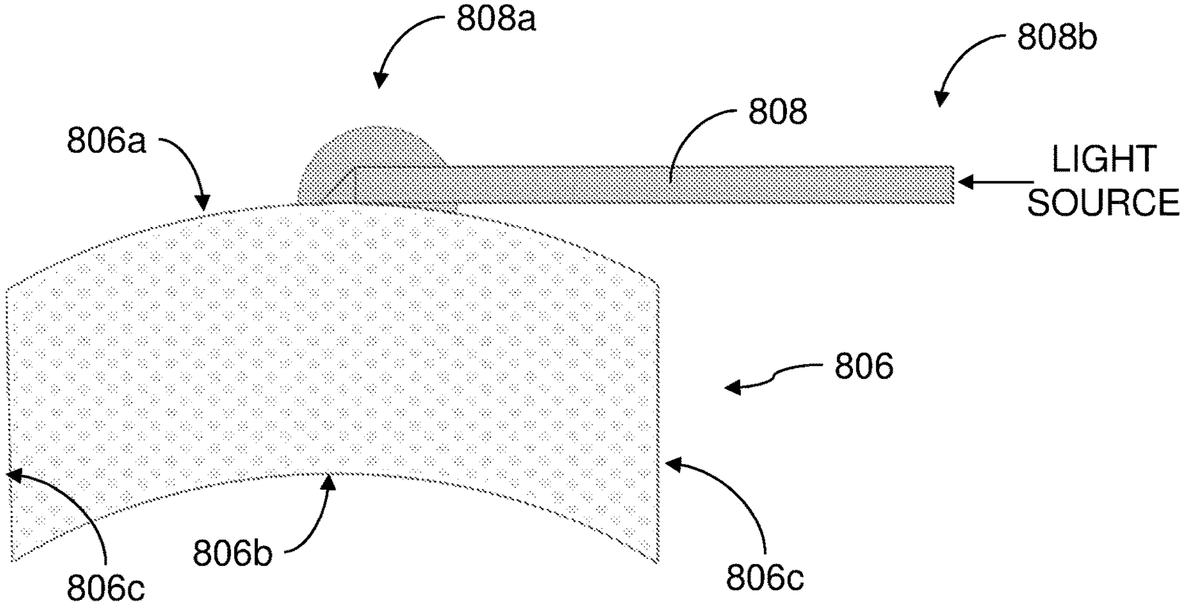
FIG. 8 illustrates an example micro-optical element for a treatment device that delivers photoactivating light uniformly to a cornea of an eye to generate cross-linking of corneal tissue, according to aspects of the present disclosure.

FIG. 8 illustrates an example micro-optical element 806 that is configured to deliver the photoactivating light uniformly to a cornea. The micro-optical element 806, for instance, may replace the micro-optical element 206 in the body of any of the treatment devices above. A proximal end 808*a* of an optical fiber 808 is coupled to the micro-optical element 806, while a distal end 808*b* of the optical fiber 808 is coupled to a light source. The optical fiber 808 terminates at the proximal end 808*a* with an angled (e.g., 90-degree) reflecting surface to direct the photoactivating light into the micro-optical element 806. A reflective coated micro-prism may be bonded to the optical fiber 808 to produce a 90-degree reflecting surface. Alternatively, a 45-degree surface may be polished into the optical fiber 808 and a reflective coating may optionally be applied. The optical fiber 808 may be bonded to the micro-optical element 806 using a bead of epoxy.

Photoactivating light travels from the light source to the micro-optical element 806 via the optical fiber 808. The micro-optical element 806 is formed from a material doped with isotropically scattering particles, such as TiO2 nanoparticles. The particles diffuse and homogenize the photoactivating light that are transmitted from the optical fiber 808. In particular, the photoactivating light might emanate from a point at an apex where the optical fiber 808 is coupled to the micro-optical element 806.

The micro-optical element 806 includes an anterior surface 806*a*, a posterior surface 806*b*, and one or more side surfaces 806*c* extending between the anterior surface 806*a* and the posterior surface 806*b*. The anterior surface 806*a* corresponds with the anterior surface of the treatment device facing away from the cornea, while the posterior surface 806*b* corresponds with the posterior surface of the treatment device facing toward the cornea. The photoactivating light is therefore transmitted through the posterior surface 806*b* to the cornea. As such, the anterior surface 806*a* and the one or more side surfaces 806*c* may be coated with a highly reflective coating. The coating reduces the loss of photoactivating light through the anterior surface 806*a* and the one or more side surfaces 806*c* and keeps the photoactivating light from reaching tissue beyond the targeted treatment areas of the cornea. Additionally, a reflective or absorbing coating may be applied to parts of the posterior surface 806*b* to produce a mask that defines a pattern, such as a circle or annulus, of photoactivating light to be applied to the targeted treatment areas of the cornea.

Figure 9A:
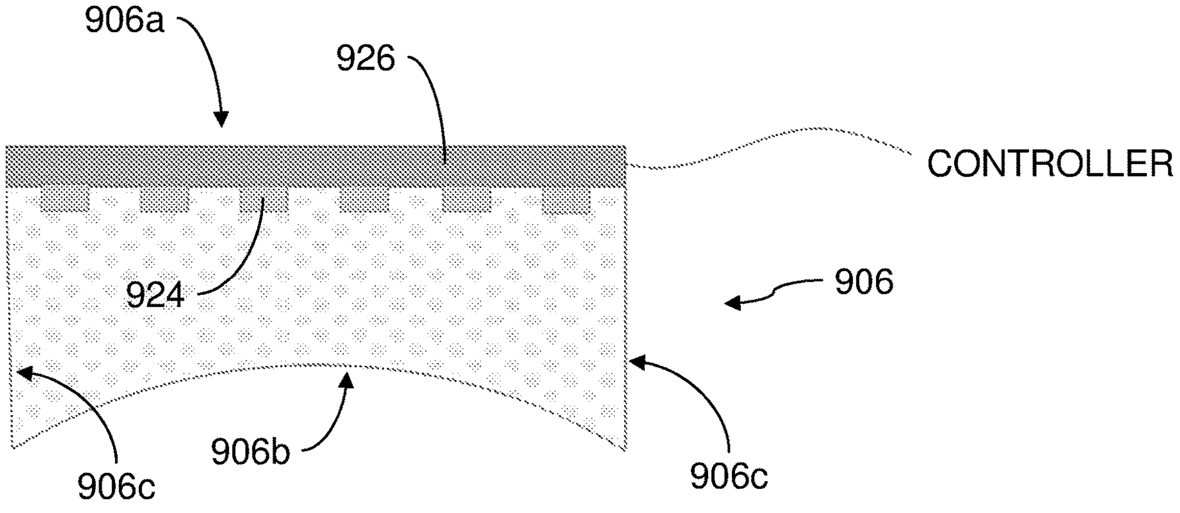
FIG. 9A illustrates a view of another example micro-optical element for a treatment device that employs micro-LEDs to deliver photoactivating light to a cornea of an eye to generate cross-linking of corneal tissue, according to aspects of the present disclosure.
Figure 9B:
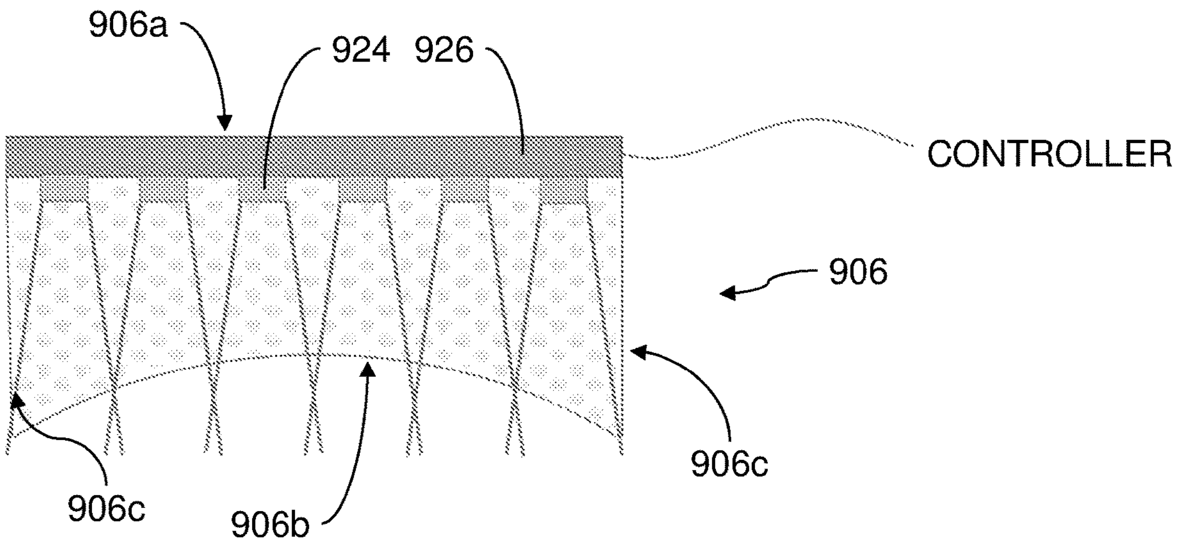
FIG. 9B illustrates another view of the example micro-optical element shown in FIG. 9A.

FIGS. 9A-B illustrate another example micro-optical element 906 that is configured to deliver photoactivating light to a cornea. The micro-optical element 906, for instance, may replace the micro-optical element 206 in the body of the treatment devices above and eliminate the need for the optical fiber 208, and the external light source. The micro-optical element 906 includes one or more micro-LEDs 924, which may be coupled to an external controller. The micro-optical element 906 includes an anterior surface 906*a*, a posterior surface 906*b*, and one or more side surfaces 906*c* extending between the anterior surface 906*a* and the posterior surface 906*b*. The photoactivating light is transmitted through the posterior surface 906*b* to the cornea. The one or more micro-LEDs 924 may be integrated into or otherwise coupled to the anterior surface 906*a*. For instance, an array of the micro-LEDs 924 may be assembled on a flex circuit 926, which may subsequently be sealed to the micro-optical element 906 with a thin, smooth layer of epoxy. All of the micro-LEDs 924 may be activated to produce a full illumination pattern as shown in FIG. 9B. Alternatively, a subset of the micro-LEDs 924 may be activated to produce smaller illumination pattern for treatment of smaller areas of the cornea. For instance, the subset of the micro-LEDs 924 may provide an illumination pattern with a substantially circular shape having a diameter of approximately 4 mm to treat myopia, or the subset of the micro-LEDs 924 may provide an illumination pattern with a substantially annular shape to treat hyperopia or presbyopia. In an alternative embodiment, the array of micro-LEDs 924 may be replaced by an OLED array, which may be flexible and may contain a phosphor layer to convert the OLED emission to other wavelengths such as UV.

Like the micro-optical element 806 above, the micro-optical element 906 may be formed from a material doped with isotropically scattering particles, such as TiO2 nanoparticles. The particles diffuse and homogenize the photoactivating light for delivery to the cornea. For instance, employing a doped material may be particularly suitable to deliver a uniform, homogenous illumination pattern having a substantially circular shape.

Alternatively, the micro-optical element 906 may be formed from a material without any such doping (e.g., with TiO2 nanoparticles). For instance, it may be more suitable to deliver an illumination pattern having an annular shape with a material that does not scatter light between the micro-LEDs 924 and the cornea.

Additionally, the anterior surface 906*a* and the one or more side surfaces 906*c* may be coated with a highly reflective coating. The coating reduces the loss of photoactivating light through the anterior surface 906*a* and the one or more side surfaces 906*c* and keeps the photoactivating light from reaching tissue beyond the targeted treatment areas of the cornea.

Figure 10:
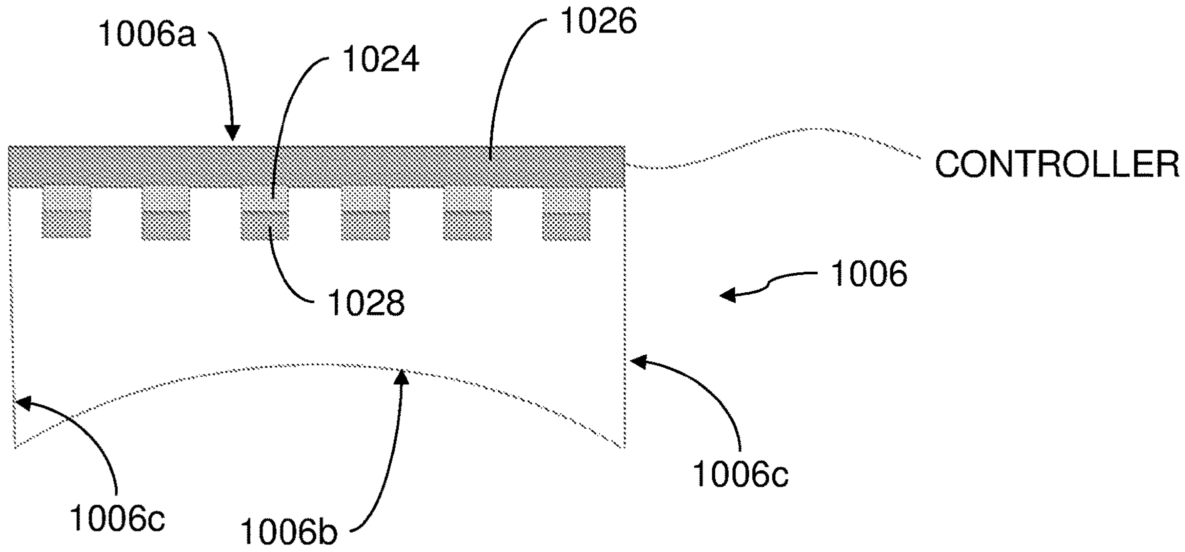
FIG. 10 illustrates another example micro-optical element for a treatment device that employs a 21) array of micro-LEDs and a micro-lens array to deliver photoactivating light to a cornea of an eye to generate cross-linking of corneal tissue according to a custom pattern, according to aspects of the present disclosure.

FIG. 10 illustrates yet another example micro-optical element 1006 that is configured to deliver photoactivating light to a cornea. The micro-optical element 1006, for instance, may replace the micro-optical element 206 in the body of the treatment devices above and eliminate the need for the optical fiber 208, and the external light source. The micro-optical element 1006 includes a 2D array of micro-LEDs 1024 that can provide customized illumination patterns for treatment of specific areas of the cornea. The microoptical element 1006 includes an anterior surface 1006*a*, a posterior surface 1006*b*, and one or more side surfaces 1006*c* extending between the anterior surface 1006*a* and the posterior surface 1006*b*. The photoactivating light is transmitted through the posterior surface 1006*b* to the cornea. The array of micro-LEDs 1024 may be assembled on a flex circuit 1026 which is disposed along the anterior surface 1006*a*. The array of micro-LEDs 1024 may also be coupled to an external controller.

The micro-LEDs 1024 are in optical communication with a micro-lens array 1028, such as a silicon micro-lens array, which allows the light from each micro-LED 1024 to be manipulated and focused in a controlled way onto the cornea. All of the micro-LEDs 1024 may be activated or a subset of the micro-LEDs 1024 may be activated. Selectively activating/deactivating individual micro-LEDs 1024 allows the illumination pattern to be programmed in a customized manner, enabling the creation of variously sized spots, rings, or other patterns. Furthermore, the ability to address each micro-LED 1024 individually allows the light dose to be spatially customized, where some micro-LEDs 1024 can be selectively activated at higher intensity or for longer durations than other micro-LEDs 1024.

Sufficient homogenization of the photoactivating light can be achieved by partially overlapping the focal spots from each micro-LED 1024 on the cornea. Optionally, the micro-optical element 1006 may be formed from a material doped with isotropically scattering particles, such as TiO2 nanoparticles, to diffuse and homogenize the photoactivating light. In an alternative embodiment, the array of micro-LEDs 1024 may be replaced by an OLED array, which may be flexible and may contain a phosphor layer to convert the OLED emission to other wavelengths such as UV.

Figure 11:
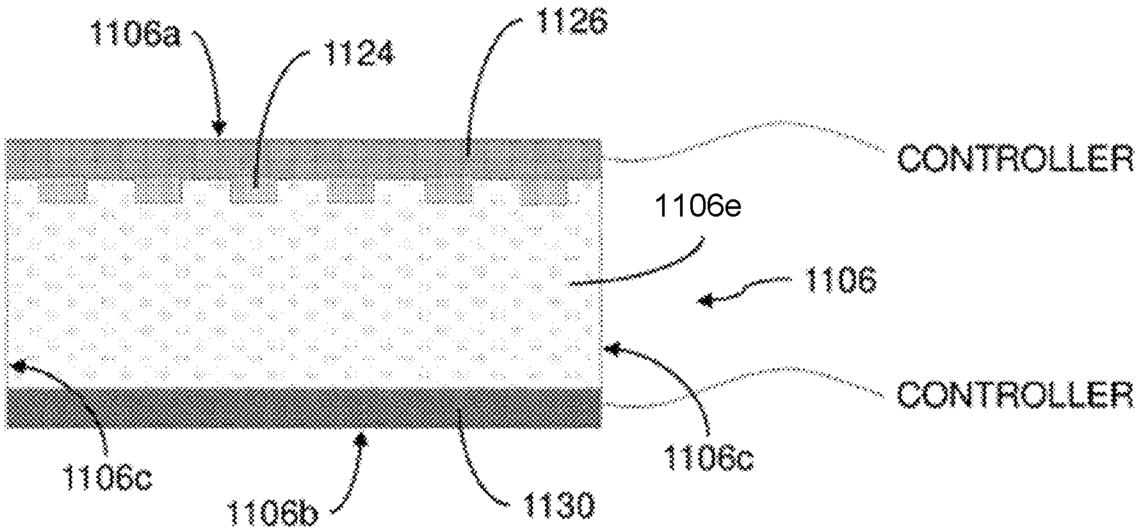
FIG. 11 illustrates a further example micro-optical element for a treatment device that employs an array of micro-LEDs and a spatial light modulator to deliver photoactivating light to a cornea of an eye to generate cross-linking of corneal tissue according to a custom pattern, according to aspects of the present disclosure.

FIG. 11 illustrates a further example micro-optical element 1106 that is configured to deliver photoactivating light to a cornea according to a custom illumination pattern. The micro-optical element 1106 includes an array of micro-LEDs 1124 that emits the photoactivating light. The micro-optical element 1106 includes an anterior surface 1106*a*, a posterior surface 1106*b*, and one or more side surfaces 1106*c* extending between the anterior surface 1106*a* and the posterior surface 1106*b*. The photoactivating light is transmitted through the posterior surface 1106*b* to the cornea. The array of micro-LEDs 1124 may be assembled on a flex circuit 1126 which is disposed along the anterior surface 1106*a*. The micro-optical element 1106 includes a spatial light modulator 1130, such as a liquid crystal light modulator, disposed along the posterior surface 1106*b*. The micro-LEDs 1124 illuminate the spatial light modulator 1130 after passing through a region 1106*e* doped with isotropic scattering particles, such as TiO2 nanoparticles. The spatial light modulator 1130 contains individually addressable pixels that can block or transmit the photoactivating light. By selectively activating or deactivating the pixels, a customized pixelated treatment pattern can be generated. The spatial light modulator 1130 may provide various levels of transmission rather than a binary "on/off" setting, allowing the light dose to be spatially customized as well. The array of micro-LEDs 1124 and the spatial light modulator 1130 may be coupled to an external controller. In an alternative embodiment, the array of micro-LEDs 1124 may be replaced by an OLED array, which may be flexible and may contain a phosphor layer to convert the OLED emission to other wavelengths such as UV.

Figure 12:
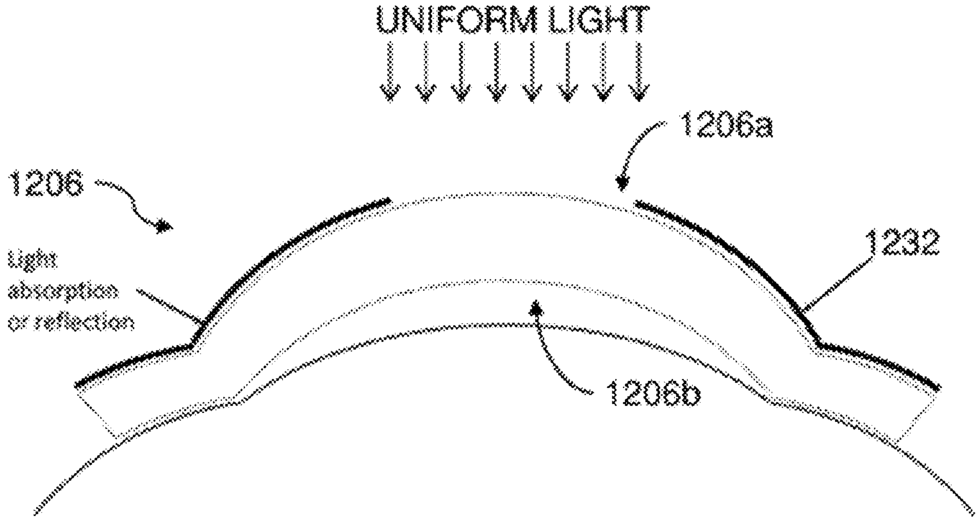
FIG. 12 illustrates another example micro-optical element for a treatment device that employs one or more materials to define light absorption or reflection pattern(s) to deliver photoactivating light to a cornea of an eye to generate cross-linking of corneal tissue according to a predetermined pattern, according to aspects of the present disclosure.

FIG. 12 illustrates another example micro-optical element 1206. A uniform photoactivating light may be generated according to the approaches described above (e.g., with retCrence to FIGS. 8, 9A-B). Alternatively, a uniform photoactivating light may be generated with a flat panel display employing a liquid crystal display (LCD), LED, OLED, or micro-LED. The flat panel display may be mounted on a goggles-like device placed over a subject's face to position the flat panel display at a distance from the eyes. Alternatively, a uniform photoactivating light may be generated by another optical system, such as the KXL SYSTEM or MOSAIC SYSTEM from Avedro, Inc. (Waltham, Massachusetts), and through the micro-optical element 1206. The micro-optical element 1206 is then configured to transmit or otherwise deliver the uniform photoactivating light to a cornea according to any predetermined illumination pattern. Additionally, the micro-optical element 1206 may employ the approaches above to deliver oxygen (e.g., with reference to FIGS. 2-7).

One or more materials that define light absorption or reflection pattern(s) 1232 may be embedded within, coated on, or otherwise applied to the micro-optical element 1206. The light absorption or reflection pattern(s) 1232 can block or otherwise prevent sections of the micro-optical element 1206 from delivering the photoactivating light to the cornea. Conversely, the remaining sections of the micro-optical element 1206 define the pattern for delivery of the photoactivating light to the cornea and corresponding cross-linking activity. As shown in FIG. 12, for instance, uniform photoactivating light is generated and directed to an anterior surface 1206*a* of the micro-optical element 1206. The light absorption or reflection pattern(s) 1232 provide a mask that blocks the uniform photoactivating light from passing through particular sections (e.g., outside a central zone) of the micro-optical element 1206 to a posterior surface 1206*b* and the cornea.

Figure 13:
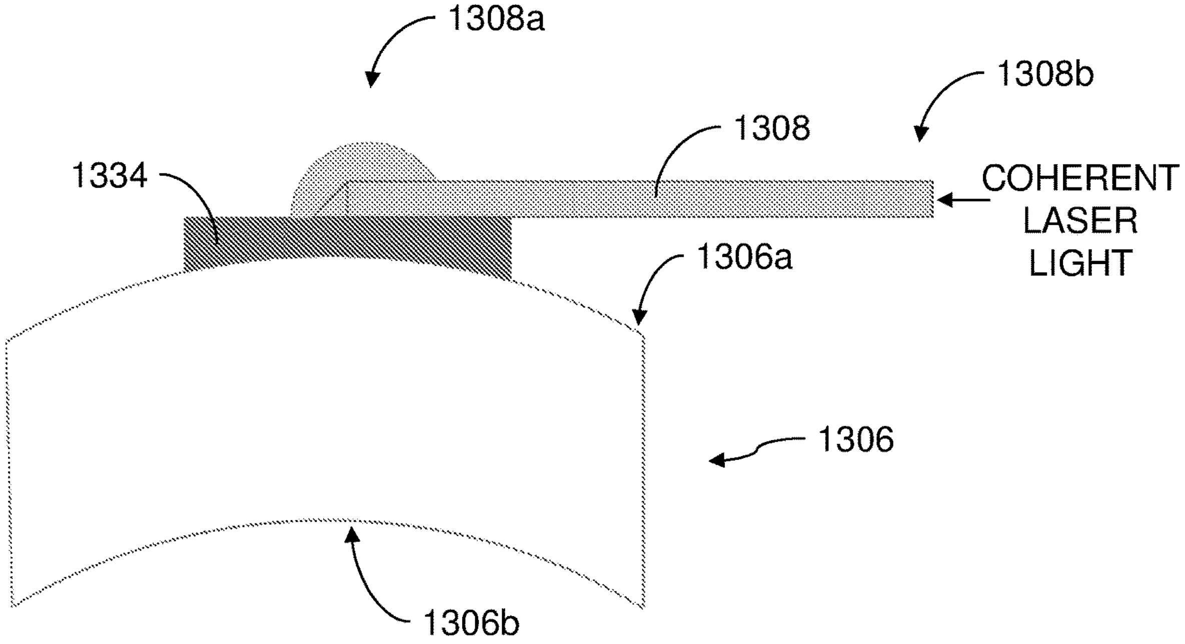
FIG. 13 illustrates yet another example micro-optical element for a treatment device that employs a diffractive optical element (DOE) to deliver photoactivating light to a cornea of an eye to generate cross-linking of corneal tissue according to a predetermined pattern, according to aspects of the present disclosure.

FIG. 13 illustrates yet another example micro-optical element 1306 that is configured to deliver uniform photoactivating light to a cornea according to any predetermined illumination pattern. A distal end 1308*b* of an optical fiber 1308 is coupled to a light source for a coherent laser. Meanwhile, a proximal end 1308*a* of the optical fiber 1308 terminates at a diffractive optical element (DOE) 1334 positioned on an anterior surface 1306*a* of the micro-optical element 1306. The DOE 1334, for instance, may be coupled to the micro-optical element 1306 using an epoxy. The optical fiber 1308 delivers the light from the distal end 1308*b* to the proximal end 1308*a*. The proximal end 1308*a* has an angled reflecting surface to direct the light toward the DOE 1334. A reflective coated micro-prism may be bonded to the optical fiber 1308 to produce the angled reflecting surface, or the reflecting surface may be directly angle-polished into the optical fiber 1308 itself. The DOE 1334 may be etched to the optical fiber 1308 or the micro-prism.

The DOE 1334 is configured to generate the illumination pattern for delivery through a posterior surface 1306*b* of the micro-optical element 1306 and to the cornea. The size of the illumination pattern can be controlled through the distance between the optical fiber 1308 and the eye and/or via additional optics (e.g., as a gradient-index (GRIN) lens). In this embodiment, diffusing materials are not employed in the micro-optical element 1306. Additionally, the micro-optical element 1306 may employ the approaches above to deliver oxygen (e.g., with reference to FIGS. 2-7).

In view of the foregoing, embodiments employ a treatment micro-device (e.g., form factor of a scleral contact lens) that can integrate delivery of a cross-linking agent, photoactivating light, and oxygen for a cross-linking procedure. For instance, embodiments can:

- provide enhanced oxygen delivery to the cornea by employing selected materials, micro-channels, and/or integrated micro-tubing;
- provide more uniform delivery of photoactivating light to the cornea by employing optical fibers coupled to an external light source and/or micro-LED's integrated directly with the treatment micro-device;
- provide controllable delivery of photoactivating light to the cornea by employing individually addressable micro-LED arrays and/or spatial light modulators, which may be integrated directly with the treatment micro-device; and/or
- provide for delivery of any predetermined pattern of photoactivating light to the cornea by employing light absorption and/or reflection pattern(s), and/or employing a diffractive optical element (DOE) with fiber-coupled laser delivery.

Advantageously, the embodiments do not require the use of an eyelid speculum to hold the eye open throughout the procedure and as such reduce patient discomfort associated with use eyelid speculum. Additionally, the patient may be seated upright during the procedure. Such embodiments can simplify clinical workflow by requiring substantially less intervention and/or monitoring by the practitioner during the cross-linking procedure, e.g., to ensure proper delivery of photoactivating light, proper eye hydration, etc. Furthermore, capital cost may also be significantly reduced compared to systems that require complex optics, electronics, sophisticated eye tracking technology, etc.

In some procedures, a fluid or topical anaesthetic may be applied between the surface of the cornea 2 and the treatment devices above to enhance patient comfort during a procedure. The fluid or topical anesthetic may have a viscosity that allows the treatment device to maintain its position on the eye 1 (a Inore viscous fluid might be more effective in keeping the treatment device in position than a less viscous fluid). Procedures with short irradiance times of less than about an hour, however, might forego the use of the fluid or topical anaesthetic to enhance comfort or maintain position.

As described above, according to some aspects of the present disclosure, some or all of the steps of the above-described and illustrated procedures can be automated or guided under the control of a controller (e.g., the controller 120). Generally, the controllers may be implemented as a combination of hardware and software elements. The hardware aspects may include combinations of operatively coupled hardware components including microprocessors, logical circuitry, communication/networking ports, digital filters, memory, or logical circuitry. The controller may be adapted to perform operations specified by a computer-executable code, which may be stored on a computer readable medium.

As described above, the controller may be a programmable processing device, such as an external conventional computer or an on-board field programmable gate array (FPGA) or digital signal processor (DSP), that executes software, or stored instructions. In general, physical processors and/or machines employed by embodiments of the present disclosure for any processing or evaluation may include one or more networked or nonnetworked general purpose computer systems, microprocessors, field programmable gate arrays (FPGA's), digital signal processors (DSP's), micro-controllers, and the like, programmed according to the teachings of the example embodiments of the present disclosure, as is appreciated by those skilled in the computer and software arts. The physical processors and/or machines may be externally networked with the image capture device(s), or may be integrated to reside within the image capture device. Appropriate software can be readily prepared by programmers of ordinary skill based on the teachings of the example embodiments, as is appreciated by those skilled in the software art. In addition, the devices and subsystems example embodiments can be implemented by the preparation of application-specific integrated circuits or by interconnecting an appropriate network of conventional component circuits, as is appreciated by those skilled in the electrical art(s). Thus, the example embodiments are not limited to any specific combination of hardware circuitry and/or software.

Stored on any one or on a combination of computer readable media, the example embodiments of the present disclosure may include software for controlling the devices and subsystems of the example embodiments, for driving the devices and subsystems of the example embodiments, for enabling the devices and subsystems of the example embodiments to interact with a human user, and the like. Such software can include, but is not limited to, device drivers, firmware, operating systems, development tools, applications software, and the like. Such computer readable media further can include the computer program product of an embodiment of the present disclosure for performing all or a portion (if processing is distributed) of the processing performed in implementations. Computer code devices of the example embodiments of the present disclosure can include any suitable interpretable or executable code mechanism, including but not limited to, scripts, interpretable programs, dynamic link libraries (DLLs), Java classes and applets, complete executable programs, and the like. Moreover, parts of the processing of the example embodiments of the present disclosure can be distributed for better performance, reliability, cost, and the like.

Common forms of computer-readable media may include, for example, a floppy disk, a flexible disk, hard disk, magnetic tape, any other suitable magnetic medium, a CDROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the present disclosure. It is also contemplated that additional embodiments according to aspects of the present disclosure may combine any number of features from any embodiments described herein.

What is claimed is:

1. A micro-device for corneal cross-linking treatment, comprising:

a body including an outer portion and an inner portion, the inner portion coupled to the outer portion, the outer portion being disposed about a periphery of the inner portion, the inner portion being shaped such that, when the body is positioned against a surface of an eye, the outer portion contacts the surface of the eye and the inner portion defines a chamber over a cornea of the eye;

an illumination system including a micro-optical element coupled to the body; and a spatial light modulator coupled to the body and including individually addressable pixels configured to block or transmit photoactivating light and generate a customized pixelated treatment pattern, wherein the micro-optical element including a plurality of micro-light emitting diodes (micro-LEDs) is located on an anterior surface of the body and is configured to direct photoactivating light through the inner portion of the body to the cornea of the eye when the body is positioned against the surface of the eye, the photoactivating light generating cross-linking activity with a cross-linking agent applied to the cornea, wherein the spatial light modulator is located on a posterior surface of the body, and wherein a region including a light diffusing material is disposed between the plurality of micro-LEDs and the spatial light modulator.

2. The micro-device of claim 1, wherein the micro-optical element is coupled to the inner portion of the body and directs the photoactivating light through the inner portion and the chamber to the cornea of the eye.

3. The micro-device of claim 1, wherein the body is formed at least partially from an oxygen-permeable material, the oxygen-permeable material allowing oxygen to enter the chamber when the body is positioned against the surface of the eye.

4. The micro-device of claim 1, wherein the body includes one or more micro-channels extending to the chamber, the one or more micro-channels configured to allow oxygen to enter the chamber when the body is positioned against the surface of the eye.

5. The micro-device of claim 1, further comprising an oxygen delivery mechanism coupled to the body and configured to deliver oxygen to the chamber when the body is positioned against the surface of the eye.

6. The micro-device of claim 5, wherein the oxygen delivery mechanism includes one or more micro-channels coupled to an oxygen supply and configured to deliver the oxygen from the oxygen supply to the chamber when the body is positioned against the surface of the eye, and the body includes one or more vents extending from the chamber and configured to allow the oxygen to exit the chamber.

7. The micro-device of claim 6, wherein the oxygen delivery mechanism includes a flexible tube coupling the oxygen supply to the micro-channels, and the flexible tube is further configured to deliver the cross-linking agent to the chamber.

8. The micro-device of claim 1, wherein the body includes one or more side channels extending into the chamber at the periphery of the inner portion and one or more vents extending from the chamber at the periphery of the inner portion, the one or more side channels configured to be coupled to an oxygen source and to deliver oxygen from the oxygen source to the chamber when the body is positioned against the surface of the eye, the one or more vents configured to allow the oxygen to exit the chamber after the oxygen flows over the cornea of the eye.

9. The micro-device of claim 1, wherein the micro-LEDs are in optical communication with a micro-lens array configured to allow the light from each micro-LED to be manipulated and focused onto the cornea.

10. The micro-device of claim 1, wherein the micro-LEDs are assembled on a flex circuit.

11. The micro-device of claim 1, further comprising a controller configured to selectively activate a subset of the micro-LEDs to produce a pattern of the photoactivating light with a substantially circular shape.

12. The micro-device of claim 11, wherein the substantially circular shape has a diameter of approximately 4 mm.

13. The micro-device of claim 1, wherein a controller is configured to selectively activate a subset of the micro-LEDs to produce a pattern of the photoactivating light with a substantially annular shape.

14. The micro-device of claim 1, wherein a controller is configured to selectively activate some of the micro-LEDs at higher intensity or for longer durations than other of the micro-LEDs.

15. The micro-device of claim 1, wherein the micro-optical element is formed from a material doped with isotropically scattering particles to homogenize the photoactivating light from the micro-LEDs.

16. The micro-device of claim 1, wherein the micro-optical elements includes a reflective coating configured to reflect the photoactivating light within the chamber to the cornea of the eye.

17. The micro-device of claim 1, wherein the micro-light emitting diodes (micro-LEDs) are configured to be selectably illuminated by a controller to provide a pattern of the photoactivating light.

18. The micro-device of claim 1, wherein the spatial light modulator is configured to receive the photoactivating light from the micro-LEDs and produce a pattern of the photoactivating light defined by pixels.

19. A micro-device for corneal cross-linking treatment, comprising:

a body including an outer portion and an inner portion, the inner portion coupled to the outer portion, the outer portion being disposed about a periphery of the inner portion, the inner portion being shaped such that, when the body is positioned against a surface of an eye, the outer portion contacts the surface of the eye and the inner portion defines a chamber over a cornea of the eye;

an illumination system including a micro-optical element coupled to the body; and a spatial light modulator coupled to the body and including individually addressable pixels configured to block or transmit photoactivating light and generate a customized pixelated treatment pattern, wherein the micro-optical element is located on an anterior surface of the body and is configured to direct photoactivating light through the inner portion of the body to the cornea of the eye when the body is positioned against the surface of the eye, the photoactivating light generating cross-linking activity with a cross-linking agent applied to the cornea, wherein the spatial light modulator is located on a posterior surface of the body, and wherein a region including a light diffusing material is disposed between the micro-optical element and the spatial light modulator.

20. The micro-device of claim 1, wherein the light diffusing material comprises isotropic scattering particles.

* * * * *